United States Patent
Kielhorn et al.

(10) Patent No.: US 9,442,009 B2
(45) Date of Patent: Sep. 13, 2016

(54) APPARATUS AND METHOD FOR MAKING OPTICAL MEASUREMENTS OF SAMPLES

(71) Applicant: DeNovix Inc., Wilmington, DE (US)

(72) Inventors: Fernando F. Kielhorn, Wilmington, DE (US); David B. Ward, Downington, PA (US)

(73) Assignee: DeNovix, Inc., Wilmington, DE (US)

( * ) Notice: Subject to any disclaimer, the term of this patent is extended or adjusted under 35 U.S.C. 154(b) by 189 days.

(21) Appl. No.: 14/181,295

(22) Filed: Feb. 14, 2014

(65) Prior Publication Data

US 2015/0233760 A1 Aug. 20, 2015

(51) Int. Cl.
| | |
|---|---|
| *G01J 3/28* | (2006.01) |
| *G01J 3/02* | (2006.01) |
| *G01N 21/31* | (2006.01) |
| *G01N 21/03* | (2006.01) |

(52) U.S. Cl.
CPC ............ *G01J 3/0218* (2013.01); *G01N 21/03* (2013.01); *G01N 21/31* (2013.01); *G01N 2201/08* (2013.01)

(58) Field of Classification Search
CPC .. G01N 21/31; G01N 21/03; G01N 2201/08; G01N 2021/0346; G01N 21/05; G01N 21/359; G01N 2021/6484; G01J 3/42; G01J 3/02; G01J 3/0218; G01J 3/10; G01J 3/0291; G01J 3/0208
USPC ....................................... 356/326
See application file for complete search history.

(56) References Cited

U.S. PATENT DOCUMENTS

| | | | |
|---|---|---|---|
| 3,194,111 A | | 7/1965 | Saunders |
| 3,379,093 A | | 4/1968 | Ard |
| 3,486,829 A | | 12/1969 | Wilks, Jr. |
| 3,588,259 A | * | 6/1971 | Harvey .................. G01N 21/03 356/244 |
| 3,740,156 A | | 6/1973 | Heigl et al. |
| 3,937,614 A | | 2/1976 | Sodickson et al. |
| 4,038,030 A | | 7/1977 | Albright et al. |
| 4,234,254 A | | 11/1980 | Dreisbach et al. |
| 4,812,810 A | * | 3/1989 | Query .................. F25D 29/008 250/227.22 |
| 4,980,551 A | * | 12/1990 | Wong ................. G01N 21/0303 250/338.1 |
| 5,210,590 A | | 5/1993 | Landa et al. |

(Continued)

FOREIGN PATENT DOCUMENTS

| | | |
|---|---|---|
| EP | 0 706 043 B1 | 5/2000 |
| EP | 1 102 057 A1 | 5/2001 |

(Continued)

OTHER PUBLICATIONS http://www.thefreedictionary.com/housing;—http://dictionary.reference.com/browse/into;—http://www.thefreedictionary.com/through;—http://www.thefreedictionary.com/abut;—http://www.thefreedictionary.com/adjacent.*

(Continued)

*Primary Examiner* — Tarifur Chowdhury
*Assistant Examiner* — Mohamed K Amara
(74) *Attorney, Agent, or Firm* — Potter Anderson and Corroon, LLP (57) ABSTRACT

An improved apparatus and method for making optical measurements of a sample is described. In one embodiment, the apparatus is a microvolume sampling mechanism comprised of two opposing optical measurement surfaces. A sample is held by surface tension between the two opposing optical measurement surfaces. Light is transmitted through the sample and received by optical fibers, which measure the absorbance of the sample. This absorbance can be used to determine the concentration of the sample.

15 Claims, 5 Drawing Sheets

(56) References Cited

U.S. PATENT DOCUMENTS

| | | |
|---|---|---|
| 5,284,623 A | 2/1994 | Yamori et al. |
| 5,309,213 A | 5/1994 | Desjardins et al. |
| 5,597,532 A | 1/1997 | Connolly |
| 5,602,647 A | 2/1997 | Xu et al. |
| 5,739,432 A * | 4/1998 | Sinha .................. G01N 29/036 |
| | | 73/579 |
| 5,750,998 A | 5/1998 | Goldman |
| 5,774,209 A * | 6/1998 | Shestock ................ G01N 21/03 |
| | | 356/244 |
| 6,426,213 B1 | 7/2002 | Eisenson |
| 6,628,382 B2 | 9/2003 | Robertson |
| 6,809,826 B2 * | 10/2004 | Robertson .............. B82Y 15/00 |
| | | 356/246 |
| 6,841,132 B2 | 1/2005 | Samsoondar |
| 6,897,069 B1 | 5/2005 | Jarvis et al. |
| 7,224,448 B2 | 5/2007 | Ji |
| 7,259,846 B2 | 8/2007 | Schembri et al. |
| 7,277,167 B2 | 10/2007 | Schembri et al. |
| 7,365,852 B2 | 4/2008 | Schleifer |
| 7,369,226 B1 | 5/2008 | Hewitt |
| 7,375,815 B2 | 5/2008 | Kralik |
| 7,397,036 B2 * | 7/2008 | Robertson ............ G01N 21/645 |
| | | 250/364 |
| 7,593,101 B2 | 9/2009 | Yakimoski et al. |
| 7,623,225 B2 | 11/2009 | Robertson, Jr. et al. |
| 7,688,439 B2 | 3/2010 | Tsai et al. |
| 7,808,641 B2 | 10/2010 | Salerno et al. |
| 7,872,749 B2 | 1/2011 | Robertson et al. |
| 7,969,575 B2 | 6/2011 | Zuo |
| 8,004,670 B2 | 8/2011 | Juhl |
| 8,064,051 B2 | 11/2011 | Juhl |
| 8,189,199 B2 * | 5/2012 | Robertson, Jr. ............ G01J 3/02 |
| | | 356/246 |
| 8,208,145 B2 | 6/2012 | Large et al. |
| 8,223,338 B2 | 7/2012 | Robertson, Jr. et al. |
| 8,646,344 B2 * | 2/2014 | Israelachvili ............. G01N 3/04 |
| | | 73/864.91 |
| D739,771 S * | 9/2015 | Jablonski .................. G01J 3/00 |
| | | D10/81 |
| 2002/0022769 A1 * | 2/2002 | Smith ................ A61B 1/00052 |
| | | 600/188 |
| 2005/0226548 A1 * | 10/2005 | Durkin .................. G01N 21/31 |
| | | 385/12 |
| 2006/0109467 A1 | 5/2006 | Evans |
| 2006/0109468 A1 | 5/2006 | Evans |
| 2007/0220916 A1 * | 9/2007 | Fulton .................... F25D 23/02 |
| | | 62/389 |
| 2008/0028854 A1 | 2/2008 | Evans |
| 2009/0232448 A1 * | 9/2009 | Barmash ............. G02B 6/3504 |
| | | 385/26 |
| 2010/0128265 A1 | 5/2010 | Robertson et al. |
| 2011/0149280 A1 | 6/2011 | Juhl |
| 2012/0068846 A1 * | 3/2012 | Dalzell .................. G08B 13/08 |
| | | 340/545.1 |
| 2013/0148937 A1 * | 6/2013 | Rudenick ................. G02B 6/46 |
| | | 385/136 |

FOREIGN PATENT DOCUMENTS

| | | | |
|---|---|---|---|
| GB | 667896 | 3/1952 | |
| GB | 796745 | 6/1958 | |
| GB | 2200748 A * | 8/1988 | .......... G08B 13/186 |
| WO | WO-97/05472 A1 | 2/1997 | |
| WO | WO-97/43619 A1 | 11/1997 | |
| WO | WO-00/05336 A2 | 2/2000 | |

OTHER PUBLICATIONS

Google search results for optical fiber lamps.*

* cited by examiner

APPARATUS AND METHOD FOR MAKING OPTICAL MEASUREMENTS OF SAMPLES

BACKGROUND

1. Field

Embodiments of the claimed invention relate to optical measurements, and in particular, an apparatus and method for making optical measurements of samples.

2. Description of Related Art

Spectrometers are instruments used to measure the optical properties of light traveling through samples. These measurements can be used for a variety of purposes, such as to identify materials. Spectrometers typically include an upper arm having a first measurement surface coupled to a lower arm having a second measurement surface via a hinge. One of the measurement surfaces is coupled to a light source, while the other is coupled to a detector.

Two opposing fiber optic cables are provided on the opposing measurement surfaces. A sample is placed on the tips of the fiber optic cables of the lower measurement surface, and the upper measurement surface is brought into contact with the sample. The sample is pulled into a column by slightly moving the lower measurement surface and the upper measurement surface away from each other. Transmittance or absorbance of light is then measured through the sample at different distances of the upper measurement surface and the lower measurement surface.

Conventionally, the distance between the two measurement surfaces is controlled by a screw that protrudes from the base of the spectrometer. The screw comes in direct contact with the upper arm upon which the upper measurement surface is positioned. Thus, when the screw is moved up or down, the upper arm is directly moved up or down.

However, other methods of controlling the distance between the two measurement surfaces have been employed. U.S. Pat. No. 7,969,575 B2 to Zuo discloses an apparatus for measuring light absorption of liquid samples including an actuator configured to position the upper arm into a first measuring position. The actuator includes a step motor and a pushing rod, which when the step motor rotates, the pushing rod is moved linearly up and down. When extended upwardly, the pushing rod pushes a pushing pin, which in turn pushes another pin in the upper arm, which in turn pushes the upper arm upwardly. This positions the measuring surfaces at a particular distance apart.

U.S. Pat. No. 8,189,199 to Robertson, Jr. et al. relates to a dual sample mode spectrophotometer that selectively measures samples in either a vessel or as a surface tension retained sample held between two opposing pedestals. A lower optical fiber connector translates along the vertical direction to enable the spacing between the two optical fibers to be varied. The base plate is provided with a linear actuator that is mounted thereto so as to provide for precise movement of the lower optical fiber connector. The linear actuator comprises a motor designed to produce a rotational motion of a threaded nut which bears on a mating threaded shaft portion of the lower optical fiber holder. The rotation of the internally threaded screw against the externally threaded shaft portion causes controlled movement of the lower fiber optic connector.

SUMMARY OF THE INVENTION

The above described patents propose a variety of methods for making optical measurements. However, there still exists a need for an apparatus and method for making optical measurements of samples with greater precision. This is achieved in embodiments of the present invention, which can control the distance between two measurement surfaces with greater accuracy by using a screw and protrusion configuration. This distance between the two measurement surfaces is the key variable to determining a final concentration of a droplet via the Beer-Lambert law.

There further exists a need for an apparatus and method for making optical measurements that has improved wear and tear throughout its useful life. This is also achieved by embodiments of the present invention, which reduces wear and tear on the precision screw and on the protrusion bearing against the precision screw. Embodiments of the present invention may further employ a sapphire window instead of an optical fiber on one of the two opposing measurement surfaces, which has greater wear resistance than the end of an optical fiber.

In view of the foregoing, one aspect of the present invention provides for an improved apparatus for making optical measurements of a sample. In one embodiment, the apparatus is a microvolume sampling mechanism (i.e., spectrometer) comprised of two optical measurement surfaces, a fiber optic cable on a swing arm, and a custom optical surface fastened to the instrument base, which produces a sample containment area for low volume liquid UV-Vis absorbance measurements. The geometrical shape of the lower pedestal keeps liquid in place for measurement, ensuring no liquid column breakage and outstanding performance with colorimetric assays.

In operation, directed optical radiation is transmitted through a sample and the incident light is diminished by the absorption of light and/or the scattering of light rays. Optical characteristics are measured, and the concentration of the sample is calculated. This can be used, for example, to identify the sample or to study a chemical analyte.

Thus, one embodiment of the present invention provides an apparatus for making optical measurements of a sample. The apparatus comprises a first arm comprising a first measurement surface, a moveable second arm coupled to the first arm comprising a second measurement surface and a protrusion, and a housing coupled to the first arm comprising a motor and a precision screw. The protrusion extends from the second arm into the housing to abut the precision screw.

According to another embodiment of the present invention, a method for making optical measurements of a sample is described. The method comprises placing a sample on a first measurement surface on a first arm opposite a second measurement surface on a second arm, said second arm being coupled to a housing; adjusting a distance between the first measurement surface and the second measurement surface by rotating a screw contained entirely within the housing against a protrusion extending from the first arm into the housing; radiating light through the sample; and measuring optical properties of the sample.

Still other aspects, features and advantages of the present invention are readily apparent from the following detailed description, simply by illustrating a number of exemplary embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

An apparatus for making optical measurements of samples is described. In the following description, for purposes of explanation, numerous specific details are set forth in order to provide a thorough understanding of the exemplary embodiments. It is apparent to one skilled in the art, however, that the present invention can be practiced without these specific details or with an equivalent arrangement.

Figure 1A:
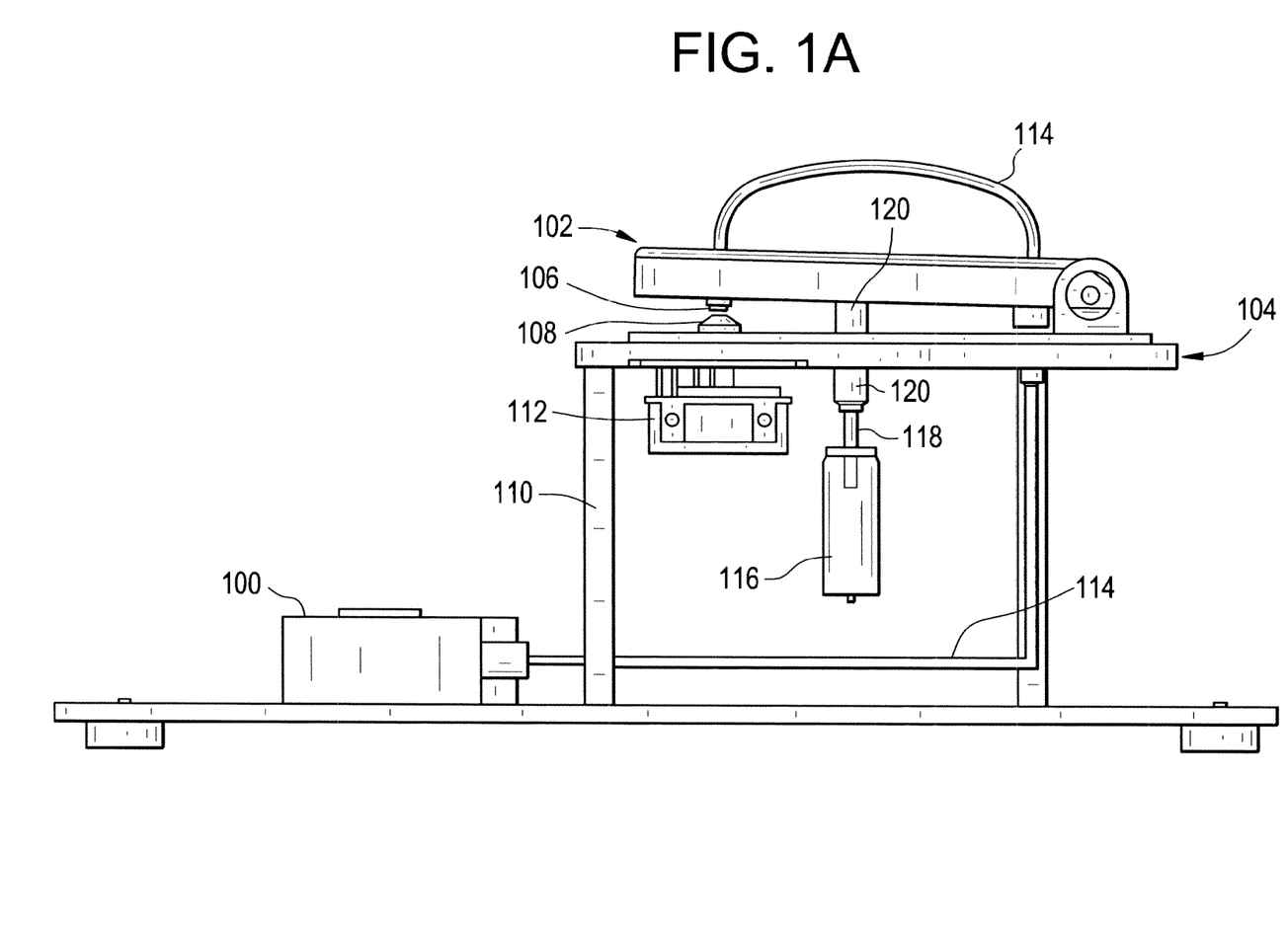
FIG. 1A is a side view of an apparatus for making optical measurements of samples in a closed, resting position according to one embodiment.
Figure 1B:
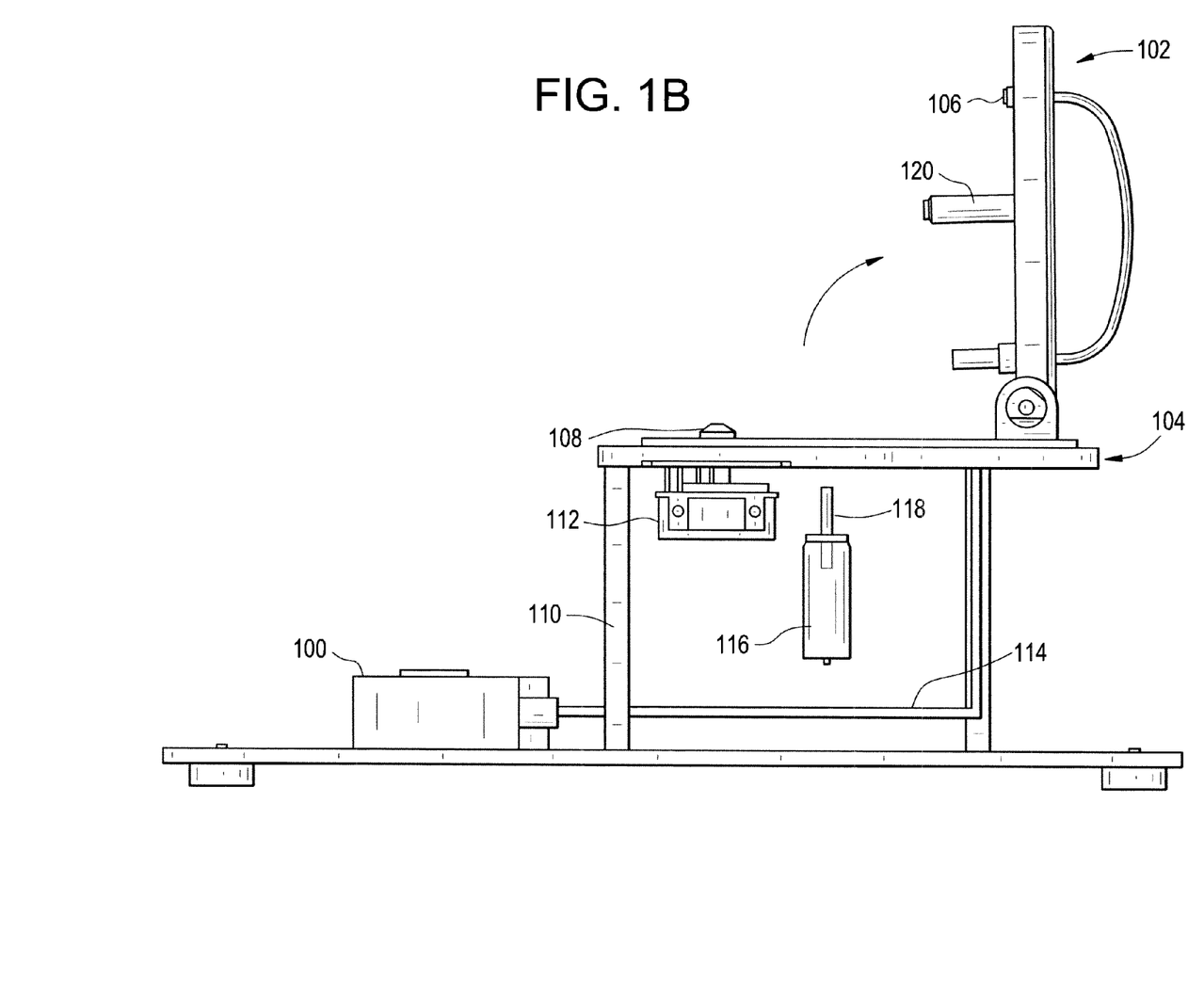
FIG. 1B is a side view of an apparatus for making optical measurements of samples in an open position according to one embodiment.

Referring now to the drawings, wherein like reference numerals designate identical or corresponding parts throughout the several views, FIG. 1A is a side view of an apparatus for making optical measurements of samples in a closed, resting position. FIG. 1B is a side view of an apparatus for making optical measurements of samples in an open position. The apparatus includes an upper arm 102 opposite to and connected to a lower arm 104 via a hinge mechanically coupled to the upper arm 102 and the lower arm 104. Thus, upper arm 102 is opened by turning through an arc of an angle sufficient for loading of a sample and cleaning upper sample surface 106 and lower sample surface 108. For example, upper arm 102 can be opened 90° from its closed, resting position, as shown in FIG. 1B. Accordingly, optical fiber 114, which passes through upper arm 102, also angularly rotates in order to come into contact with a sample in the closed, resting position, as described further herein.

The upper arm 102 has an upper sample surface 106 and the lower arm has a lower sample surface 108. The lower arm is positioned on a housing 110. The housing 110 comprises a lamp 112 below the lower sample surface 108. An optical fiber 114, e.g., a fiber optic cable, extends through the housing and into the upper arm 102. The end of optical fiber 114 is positioned within upper sample surface 106, opposing lamp 112 below the lower sample surface 108. In one embodiment, optical fiber 114 is flush with the upper sample surface 106. Optical fiber 114 can be, for example, a multi-mode fiber, a single-mode fiber, or a special purpose fiber, such as a polarization-maintaining fiber or photonic-crystal fiber. Although shown and described with respect to an optical fiber 114, it is contemplated that any other detector can replace optical fiber 114.

Figure 2A:
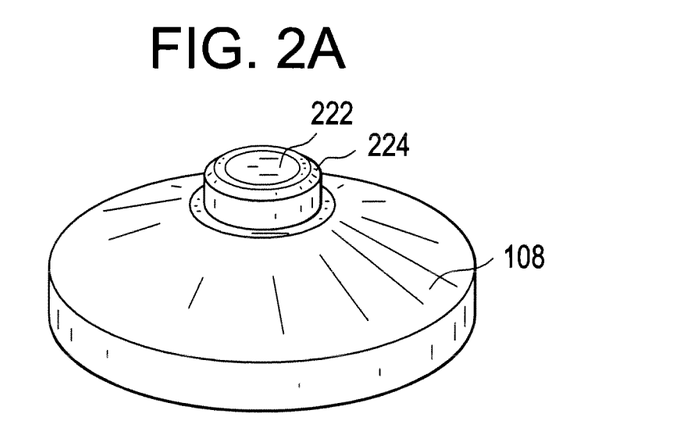
FIG. 2A is a perspective view of the lower sample surface of an apparatus for making optical measurements of samples according to one embodiment.
Figure 2B:
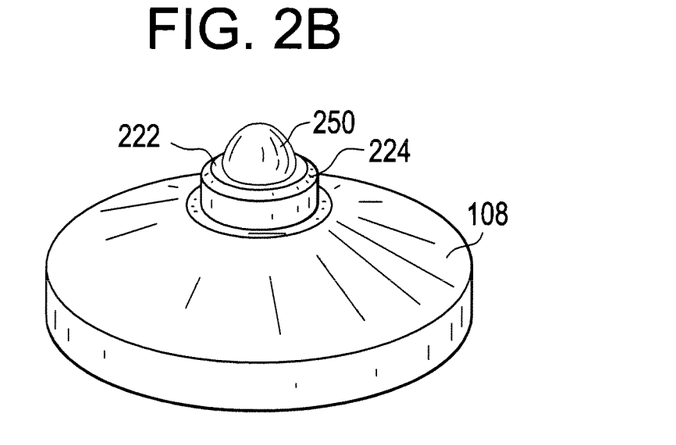
FIG. 2B is a perspective view of a droplet on the lower sample surface of an apparatus for making optical measurements of samples according to one embodiment.
Figure 2C:
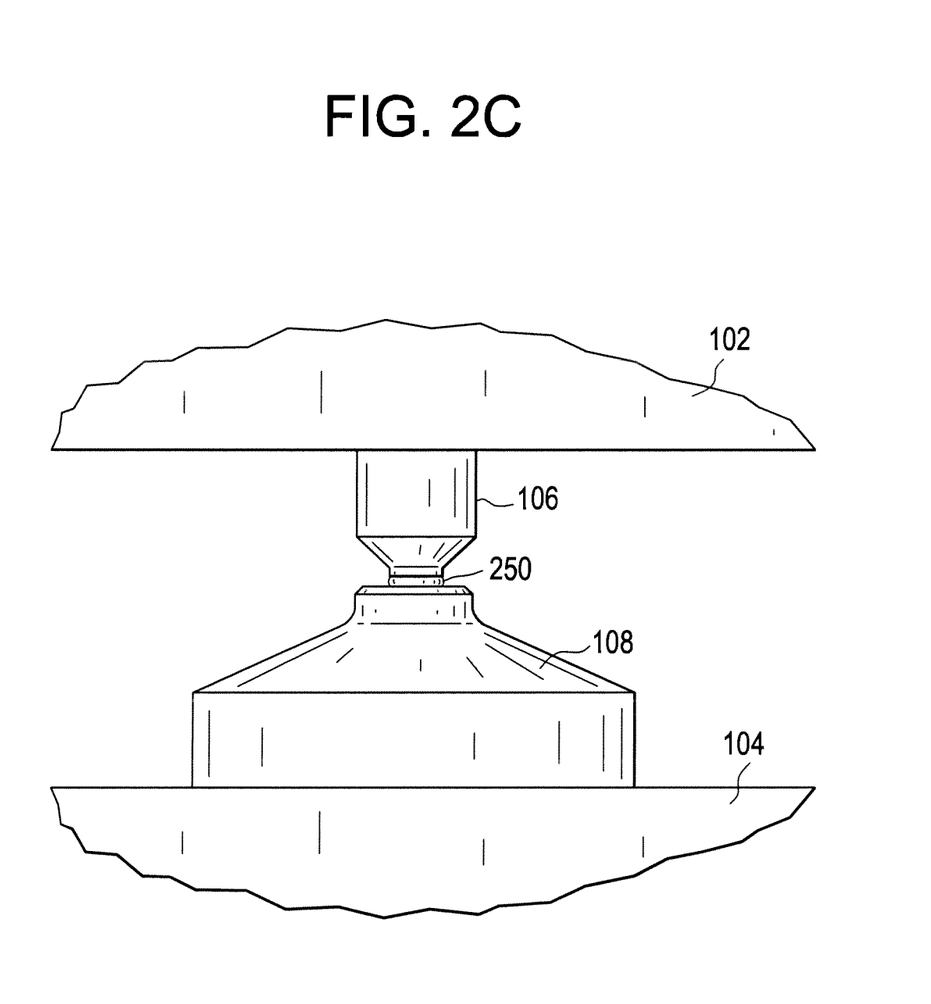
FIG. 2C is a front view of the upper and lower sample surfaces of an apparatus for making optical measurements of samples according to one embodiment.

Lower sample surface 108 may include a sapphire window, described further in detail herein with respect to FIGS. 2A-2C. In one embodiment, lower sample surface 108 having a sapphire window is coupled directly to lamp 112, such that the lens of lamp 112 is proximate to the sapphire window of lower sample surface 108. The proximity of lamp 112 to the sapphire window of lower sample surface 108 allows for a broader beam of light to enter the sample as compared to a fiber optic cable used in conventional spectrometer devices. Thus, it is made easier to align optical fiber 114 with lamp 112 compared the alignment of two fiber optic cables as in conventional spectrometer devices.

The housing 110 further comprises a motor 116 coupled to a precision screw 118. The motor 116 moves precision screw 118 up and down within the housing 110. Specifically, the motor 116 is designed to produce rotational motion of precision screw 118, which bears against a protrusion 120 extending from the upper arm 102 into a hole in housing 110. As driven by motor 116, the rotation of precision screw 118 against protrusion 120 causes the controlled translation of the upper arm 102, and consequently, the upper sample surface 106 that is housed thereon.

In one embodiment, motor 116 has an encoder that automatically moves precision screw 118 up and down to a predetermined position. In one embodiment, the motor 116 is a custom-machined Delrin slider piece as a guide that follows two metal dowels. However, the motor 116 can be any motor, linear actuator or linear translator motor.

Upper arm 102 can be moved away from lower arm 104 into an open position as shown in FIG. 1B, fully exposing lower sample surface 108. A droplet can be dispensed onto lower sample surface 108. Upper arm 102 can also be moved into a closed, resting position opposite to lower arm 104, as shown in FIG. 1A. In this position, upper sample surface 106 can contact the droplet.

Lamp 112 can be turned on in order to observe the optical properties of the droplet by optical fiber 114. Lamp 112 can be any radiation source, such as, for example, a light emitting diode (LED) or a xenon flash lamp. In one embodiment, lamp 112 is capable of delivering illumination lengths of at least 190 nm. In still another embodiment, lamp 112 has one or more filters, such as interference filters, that allow for the desired wavelength of at least 190 nm.

Data regarding the observed optical properties is transmitted through optical fiber 114 to spectrometer 100, which can itself be used to select the desired optical path lengths and perform a variety of calculations based on the measured optical properties. In another embodiment, spectrometer 100 is coupled to a computer having software to, for example, select the desired optical path lengths and perform a variety of calculations based on the measured optical properties. These measurements and calculations can be displayed and stored for later reference.

To position upper arm 102 in a measurement position, the motor 116 moves the precision screw 118, which in turn moves protrusion 120, which in turn moves the upper arm 102, thereby controlling the distance between the upper sample surface 106 and the lower sample surface 108. In one example, the motor 116 moves the precision screw 118 down, bringing upper arm 102 closer to lower arm 104 and reducing the distance between the upper sample surface 106 and the lower sample surface 108. Lamp 112 again turns on, and the optical properties of the droplet are again observed by optical fiber 114 at this second distance. Data regarding the observed optical properties is transmitted to spectrometer 100, which can perform a variety of calculations based on the measured optical properties.

Precision screw 118 remains entirely within the housing 110, even in its most extended state. This reduces wear and tear on the precision screw 118. In one embodiment, protrusion 120 has a partial or full coating, such as a PTFE coating, that reduces wear on protrusion 120, particularly where protrusion 120 comes in contact with precision screw 118. This also reduces wear shavings that can get into the thread bushing and cause erroneous readings.

FIG. 2A is a perspective view of the lower sample surface of an apparatus for making optical measurements of samples according to one embodiment. As shown, lower sample surface 108 has a window 222 upon which a sample droplet 250 is placed. In one embodiment, window 222 is minimally inset inside of the lower sample surface 108, enabling the lower surface area to hold the sample on the surface even for very low surface tension samples. In another embodiment, window 222 is flat.

In one embodiment, window 222 comprises sapphire. A sapphire window 222 allows a much broader cone of light to exit the sample surface, virtually eliminating alignment issues that can occur when using optical fiber tips. Further, the light exiting lower sample surface 108 is more uniform than that exiting an optical fiber, yielding more consistent results and therefore better measurements. The wear resistance of the sapphire is also improved as compared with the stainless steel end of an optical fiber. This is important, as the lower sample surface 108 is typically wiped after each measurement.

The geometrical shape of lower sample surface 108 and window 222 as shown in FIG. 2A keeps liquid in place for measurement. In other words, the shape of lower sample surface 108 is such that droplet 250 is confined in the optical path of optical fiber 114 within upper sample surface 106. This ensures no liquid column breakage and gives outstanding performance with colorimetric assays.

In use, droplet 250 is dispensed onto window 222 that is embedded into lower sample surface 108 fastened to lower arm 104, as shown in FIG. 2B. Droplet 250 may be dispensed onto window 222 by any method such as, for example, by pipette. When emptied by the pipette, droplet 250 spreads onto window 222 either partially or fully until it encounters edge 224 of lower sample surface 108. Edge 224 of lower sample surface 108 serves to confine droplet 250 on window 222, within the optical path of lamp 112 and optical fiber 114. Thus, droplet 250 can be any size less than or equal to the circumference of edge 224. In one embodiment, droplet 250 is as small as 1 microliter.

Upper arm 102 is moved into a closed, resting position such that upper sample surface 106 comes into contact with droplet 250, as shown in FIG. 2C. Droplet 250 is contained by its surface tension between upper sample surface 106 and lower sample surface 108. Conventionally, it is necessary to pull a droplet into a column prior to taking measurements, i.e., to move the upper sample surface and the lower sample surface slightly apart after moving the upper arm into the closed, resting position. In accordance with embodiments of the invention, it is not necessary to pull droplet 250 into a column in such a manner prior to measurement.

Light from lamp 112 radiates upward through droplet 250 and is received by optical fiber 114 in the upper sample surface 106. Optical measurements are made at this position, such as of transmittance and/or absorbance. Once the first measurement is taken, the distance between upper sample surface 106 and lower sample surface 108 is automatically reduced by an encoder in motor 116. The motor 116 moves precision screw 118 down within the housing 110. Precision screw 118 bears against a protrusion 120 extending from the upper arm 102 and into a hole in housing 110, thus moving upper arm 102 closer to lower arm 104.

The locations of the two positions and/or the travel distance between the two positions are noted. In one embodiment, these locations and distances are obtained from a sensor comprising electronics that sense movement or position of upper arm 102 with respect to lower arm 104, in the case that the sensor is located on lower arm 104. In the case that the sensor is located on upper arm 102, the sensor comprises electronics that sense movement or position of lower arm 104 with respect to upper arm 102. Such a sensor may be any type of position sensor such as, for example, a capacitance displacement sensor.

A second set of optical measurements are taken. The sample absorbance signal dictates how much the distance between the two measurement surfaces is reduced. This distance is the key variable to determine a final concentration of a droplet via the Beer Lambert law, as discussed further below. In order to determine absorbance, A, of a sample, the following equation is used:

$$A = -\log_{10}(T) = -\log_{10}(I/I_0)$$

where T is the transmittance; I the intensity of light (i.e., power per unit area) of light transmitted through the sample being measured, and $I_0$ the intensity of the incident light, in this case, the intensity of light transmitted through a blank or reference sample.

This absorbance, A, can be related to the concentration of the components being analyzed by the Beer Lambert law, which states that for solutions 1 and 2:

$$A_1/A_2 = \text{Concentration}_1/\text{Concentration}_2$$

Therefore, when compared to a blank or reference sample, the concentration of the solution of interest can be directly determined from its absorbance A.

Once the optical measurements are complete, upper arm 102 can be moved away from lower arm 104 into an open position as shown in FIG. 1B. Upper sample surface 106 and lower sample surface 108 can be cleaned by, for example, wiping the surfaces with a cloth. A new sample can be put on lower sample surface 108, and the method repeated.

Figure 3:
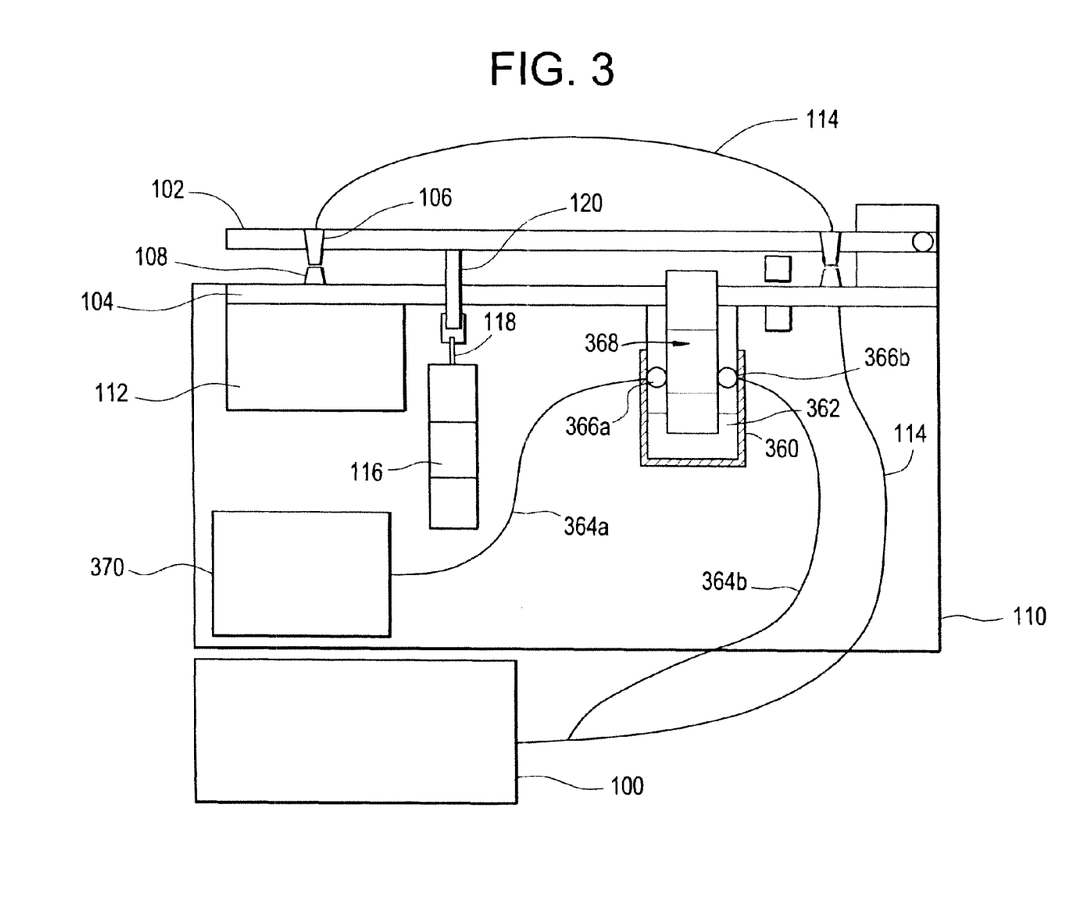
FIG. 3 is a side view of a dual-mode apparatus for making optical measurements of samples in a closed, resting position according to one embodiment.

Turning now to FIG. 3, FIG. 3 is a side view of a dual-mode apparatus for making optical measurements of samples in a closed, resting position. According to this embodiment, microvolume samples may be measured as described above, and/or larger samples can be measured via a cuvette 368. In either mode of operation, optical paths are created between two opposing light sources. The microvolume mode of operation is as described above with respect to FIGS. 1 and 2.

With respect to the cuvette mode of operation, light is transmitted from cuvette lamp 370 through cuvette lamp cable 364a to cuvette lens 366a. The transmitted light traverses the liquid sample contained in cuvette 368, and is received by an opposing cuvette lens 366b coupled to cuvette lamp cable 364b, which transmits the optical measurements to spectrometer 100. Various calculations can then be made according to the optical measurements, as described above.

In one embodiment, cuvette lenses 366a and 366b are ball lenses. Further, in one embodiment, cuvette lamp cables 364a and 364b are fiber optic cables. In another embodiment, cuvette lamp 370 is directly coupled to cuvette lens 366a, with no cuvette lamp cable 364a (not shown). Cuvette 368 is held in place by cuvette holder 360. In one embodiment, cuvette holder 360 comprises a heater 362 surrounding cuvette 368. Although described herein as a "cuvette", it is contemplated that cuvette 368 can be any type of vessel, container or tube suitable to hold liquid samples.

The present invention has been described in relation to particular examples, which are intended in all respects to be illustrative rather than restrictive. Those skilled in the art will appreciate that many different combinations of materials and components will be suitable for practicing the present invention.

Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. An apparatus for making optical measurements of a sample, the apparatus comprising:
    a first arm comprising a first measurement surface;
    a moveable second arm coupled to the first arm comprising a second measurement surface and a protrusion;
    a housing coupled to the first arm comprising a motor and a precision screw;
    a cuvette holder coupled to the first arm;
    a cuvette configured to be placed in the cuvette holder;
    a first lamp optically connected to the first measurement surface and configured to provide light to the first measurement surface;
    a second lamp optically connected to a first cuvette lens of the cuvette holder and configured to provide light to the cuvette holder; and
    a spectrophotometer optically connected to the second measurement surface and a second cuvette lens of the cuvette holder,
    wherein the protrusion extends from the second arm into the housing to abut the precision screw.

2. The apparatus of claim 1, wherein the second measurement surface comprises optical fibers.

3. The apparatus of claim 1, wherein the first measurement surface comprises a window.

4. The apparatus of claim 3, wherein the window comprises sapphire.

5. The apparatus of claim 3, further comprising a lamp abutting the window.

6. The apparatus of claim 1, wherein the motor comprises an encoder configured to automatically move the second arm.

7. A method for making optical measurements of a sample, the method comprising:
    placing the sample on the first measurement surface on the first arm opposite the second measurement surface on the moveable second arm of the apparatus of claim 1;
    adjusting a distance between the first measurement surface and the second measurement surface by rotating the precision screw contained entirely within the housing against the protrusion into the housing;
    radiating light through the sample; and
    measuring optical properties of the sample.

8. The method of claim 7, wherein the second measurement surface comprises optical fibers.

9. The method of claim 7, wherein the first measurement surface comprises a window.

10. The method of claim 9, wherein the window comprises sapphire.

11. The method of claim 9, wherein the light is radiated from a lamp abutting the window.

12. The method of claim 8, wherein the screw is rotated by a motor.

13. The method of claim 12, wherein the motor comprises an encoder configured to automatically move the second arm.

14. The apparatus of claim 1, further comprising:
    an optical fiber configured to optically connect the second measurement surface to the spectrophotometer with the second arm in a closed position.

15. The apparatus of claim 14, wherein the optical fiber comprises:
    a first portion having (i) a first end proximate to and above the second measurement surface and (ii) a second end remote from the second measurement surface and extending into the second arm; and
    a second portion having (i) a first end extending into the first arm and being aligned with the second end of the first portion with the second arm in the closed position and (ii) a second end connected to the spectrophotometer.

* * * * *